(12) United States Patent
Daigle

(10) Patent No.: US 7,054,227 B2
(45) Date of Patent: May 30, 2006

(54) METHOD FOR RECURSIVE ECHO PROCESSING IN TIME-OF-FLIGHT OR LEVEL MEASUREMENT SYSTEMS

(75) Inventor: Frank Daigle, Stouffville (CA)

(73) Assignee: Siemens Milltronics Process Instruments, Inc., Peterborough (CA)

(*) Notice: Subject to any disclaimer, the term of this patent is extended or adjusted under 35 U.S.C. 154(b) by 320 days.

(21) Appl. No.: 10/672,582

(22) Filed: Sep. 25, 2003

(65) Prior Publication Data

US 2005/0066732 A1   Mar. 31, 2005

(51) Int. Cl.
*G01N 9/24* (2006.01)
*G01S 15/08* (2006.01)

(52) U.S. Cl. .............................................. 367/99

(58) Field of Classification Search .................. 367/99, 367/908, 127; 73/290 V, 615; 342/124
See application file for complete search history.

(56) References Cited

U.S. PATENT DOCUMENTS

| | | | |
|---|---|---|---|
| 2004/0124854 A1* | 7/2004 | Slezak | 324/644 |
| 2004/0201516 A1* | 10/2004 | Lyon | 342/124 |
| 2005/0066731 A1* | 3/2005 | Wall | 73/290 V |
| 2005/0076701 A1* | 4/2005 | Lomas | 73/1.73 |

* cited by examiner

*Primary Examiner*—Daniel Pihulic
(74) *Attorney, Agent, or Firm*—Workman Nydegger

(57) ABSTRACT

A method for processing echoes in a time-of-flight ranging system or level measurement system. The method comprises a recursive descent parser which is applied to an echo profile to process and identify potential echoes. In another aspect, the method provides for processing the ring down portion of the echo profile.

21 Claims, 3 Drawing Sheets

METHOD FOR RECURSIVE ECHO PROCESSING IN TIME-OF-FLIGHT OR LEVEL MEASUREMENT SYSTEMS

FIELD OF THE INVENTION

The present invention relates to signal processing, and more particularly to a method for echo processing in level measurement or time of flight ranging systems.

BACKGROUND OF THE INVENTION

Pulse-echo acoustic ranging systems, also known as time-of-flight ranging systems, are commonly used in level measurement applications. Pulse-echo acoustic ranging systems determine the distance to a reflector (i.e. reflective surface) by measuring how long after transmission of a burst of energy pulses the echoes or reflected pulses are received. Such systems typically use ultrasonic pulses or pulsed radar or microwave signals.

Pulse-echo acoustic ranging systems generally include a transducer and a signal processor. The transducer serves the dual role of transmitting the energy pulses and receiving the reflected energy pulses or echoes. An echo profile is generated from the received energy pulses. Echo pulses are identified in the echo profile by the signal processor, and the distance or range of the object is calculated based on the transmit times of the transmitted energy pulses and the receive echo pulses.

The commonly used technique for finding echoes in an echo profile involves generating a time varying threshold or TVT curve. The TVT curve provides a baseline or line on the echo profile which is above the noise level in the echo profile. Valid echoes appear above the TVT curve. Various algorithms and techniques are known in the art for the generating the TVT curve.

A typical echo profile indicated by reference 100 is shown in FIG. 1 together with a TVT curve indicated by reference 120. The first portion of the echo profile 100 comprises a half pulse 140 which corresponds to the ring down in the transducer. The ring down corresponds to the period in which the transducer is still ringing down from the transmit pulses emitted and as such it is very difficult to detect reflected energy pulses. As shown in FIG. 1, the ring down period 140 falls underneath the TVT curve 120 and is treated as noise. Following the ring down 140, the echo profile 100 comprises a number of pulses 160, indicated individually as 160a, 160b, 160c, 160d, 160e and 16f, in FIG. 1. Using the TVT curve 12, the pulses 16a, 16b, 16c, 16d and 160e are identified as valid receive echo pulses. The last pulse 160f falls below the TVT curve 120 and is considered to comprise noise.

While the TVT technique has been used successfully in level measurement and time-of-flight ranging systems, there are shortcomings. First, generating the TVT curve can be a processor intensive process. Secondly, most TVT curves require manual adjustments to provide the best performance, and different TVT curves will work better in some situations than others. Thirdly, echoes in the ring down portion cannot be identified using a TVT curve.

Accordingly, there remains a need to provide a system and techniques which improve the processing of the reflected energy pulses or echoes.

BRIEF SUMMARY OF THE INVENTION

The present invention provides a method for echo processing in a time-of-flight or a level measurement system. According to one aspect, there is provided recursive descent parsing method for processing an echo profile. According to another aspect, the recursive descent parsing method allows processing in the ring down portion of an echo profile.

In a first aspect, the present invention provides a method for generating an echo profile in a time-of-flight ranging system, the method comprises the steps of: transmitting a transmit burst of energy to a reflective surface; receiving reflected pulses from the reflective surface, and converting the reflected pulses into echo signals for the echo profile; performing recursive descent parsing on the echo profile: determining one or more echoes in the echo profile through the recursive descent parsing.

In a further aspect, the present invention provides a method identifying echoes in an echo profile for a time-of-flight ranging system, the method comprises the steps of: transmitting a transmit burst of energy to a reflective surface; receiving reflected pulses from the reflective surface, and converting the reflected pulses into potential echoes in the echo profile; performing recursive descent parsing on the echo profile to identify valid echoes in the echo profile and eliminate invalid echoes from the echo profile.

In another aspect, the present invention provides a level measurement device for measuring a distance to a material having a surface, the level measurement device comprises: a transducer for emitting energy pulses and detecting energy pulses reflected by the surface of the material; a controller having a receiver and a transmitter; the transducer includes an input port operatively coupled to the transmitter and is responsive to the transmitter for emitting the energy pulses, and the transducer including an output port operatively coupled to the receiver for outputting reflected energy pulses coupled by the transducer; the receiver includes a converter for converting the reflected energy pulses into signals; the controller includes a program component for generating an echo profile based on the signals, the echo profile comprises potential echoes and potential noise; the controller including another program component for performing recursive descent parsing on the echo profile and for identifying one or more echoes in the echo profile.

In a yet further aspect, the present invention provides time of flight ranging system comprising: a transducer for emitting energy pulses and detecting reflected energy pulses; a controller having a receiver and a transmitter; the transducer includes an input port operatively coupled to the transmitter and is responsive to the transmitter for emitting the energy pulses, and the transducer includes an output port operatively coupled to the receiver for outputting reflected energy pulses coupled by the transducer; the receiver includes a converter for converting the reflected energy pulses into electrical signals; the controller includes a program component for generating an echo profile based on the electrical signals, the echo profile comprises potential echoes and potential noise; the controller includes another program component for performing recursive descent parsing on the echo profile and for identifying one or more echoes in the echo profile.

Other aspects and features of the present invention will become apparent to those ordinarily skilled in the art upon review of the following description of specific embodiments of the invention in conjunction with the accompanying drawings.

BRIEF DESCRIPTION OF THE DRAWINGS

Reference is next made to the accompanying drawings which show, by way of example, embodiments of the present invention and in which.

DETAILED DESCRIPTION OF EMBODIMENTS OF THE INVENTION

Figure 1:
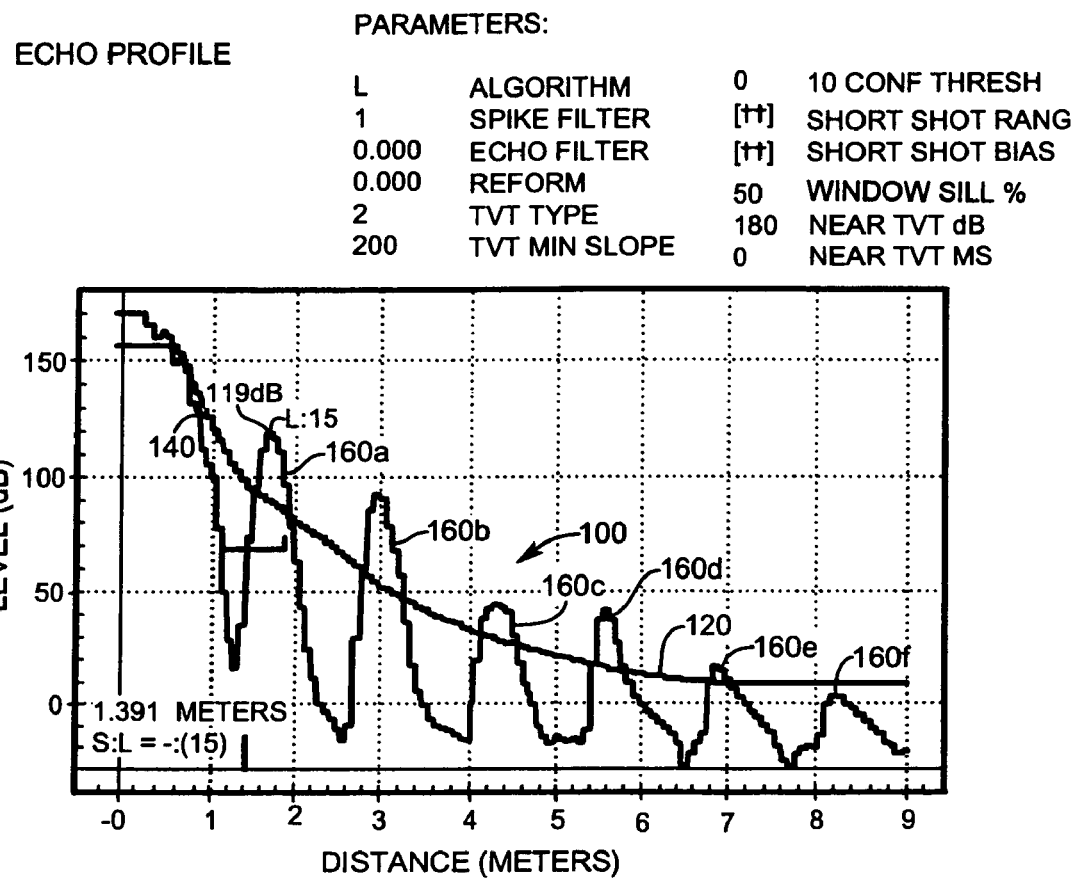
FIG. 1 is a graphic representation of an echo profile waveform and a time varying threshold curve according to the prior art.
Figure 2:
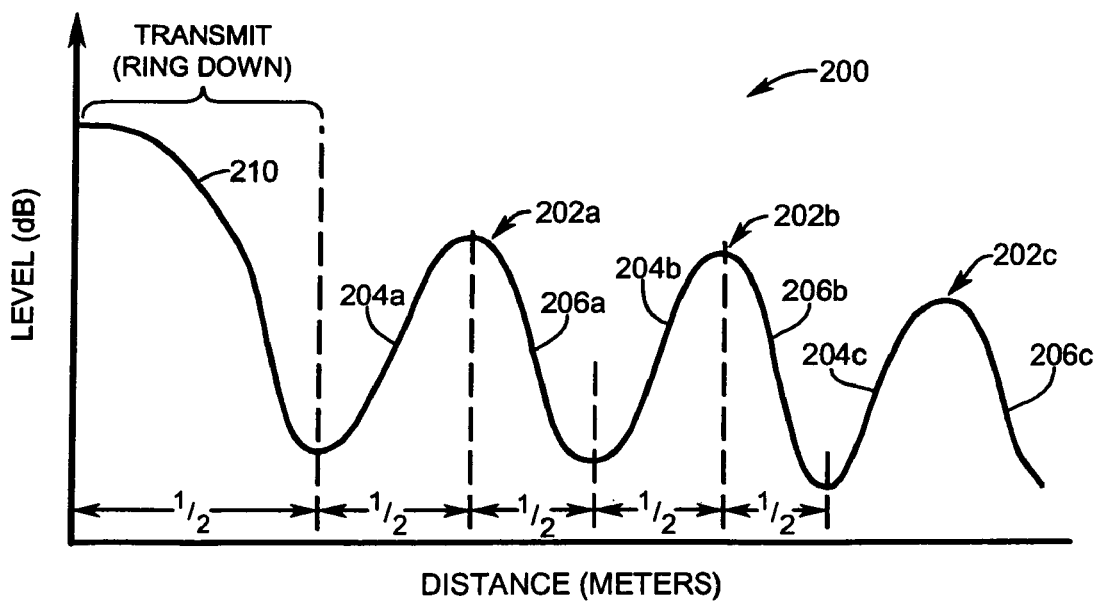
FIG. 2 is an echo profile waveform with echo pulses identified in accordance with the present invention.

Reference is made to FIG. 2 which shows in graphic form an echo profile indicated generally by reference 200.

The echo profile 200 is generated in the operation of a level measurement device (i.e. a type of time-of-flight ranging system). In known manner, the level measurement device includes a transducer (e.g. ultrasonic, microwave or radar), a controller or signal processor unit, an analog-to-digital (A/D) converter, a transmitter, a receiver, and a power supply unit. The transducer emits a transmit pulse or energy burst directed at a surface to be measured. The surface reflects the transmit energy burst and the reflected energy pulses are coupled by the transducer and converted into electrical signals. The electrical signals are applied to the receiver and sampled and digitized by the A/D converter. The signal processor, for example a microprocessor operating under firmware control, takes the digitized output and generates the echo profile 200 having a form as shown in FIG. 2. The echo profile 200 is characterized by one or more valid echoes 202, indicated individually by references 202a, 202b, 202c, . . . and which correspond to reflected energy pulses. The echo profile 200 also includes a ring-down portion 208 which corresponds to the 'ringing down' of the transducer after transmission of the energy burst or pulses. It is normally not possible to detect receive echoes during the ring down. In known manner, the controller unit executes an algorithm which uses the echo profile 200 to calculate the range, i.e. the distance to the reflective surface, from the time it takes for the reflected energy pulse to travel from the reflective surface to the transducer. From this calculation, the distance to the surface of the liquid and thereby the level of the liquid is determined The controller, e.g. microprocessor or microcontroller, is suitably programmed to perform these operations as will be within the understanding of those skilled in the art.

As will now be described in more detail, the subject invention is directed to a method or process for analyzing an echo profile for echoes or pulses. The method and processing steps as described below may be embodied in the controller as a program component or firmware.

In the context of the present invention, the echo profile 200 is treated as comprising echoes and bumps. The principle difference between echoes and bumps is that not all bumps are echoes. An echo can contain bumps, and there can be bumps within bumps, but an echo cannot contain other echoes. The bumps are typically a result of noise or quantization error in the generation of the echo profile.

According to one aspect of the invention, a recursive descent parsing technique is provided for separating echoes from noise, i.e. bumps, in the echo profile. The technique uses recursion to compare a PARENT BUMP with a CHILD BUMP and determine the nature of the PARENT BUMP. By following an iterative process the PARENT BUMP is identified as an echo or as noise in the echo profile.

Figure 3:
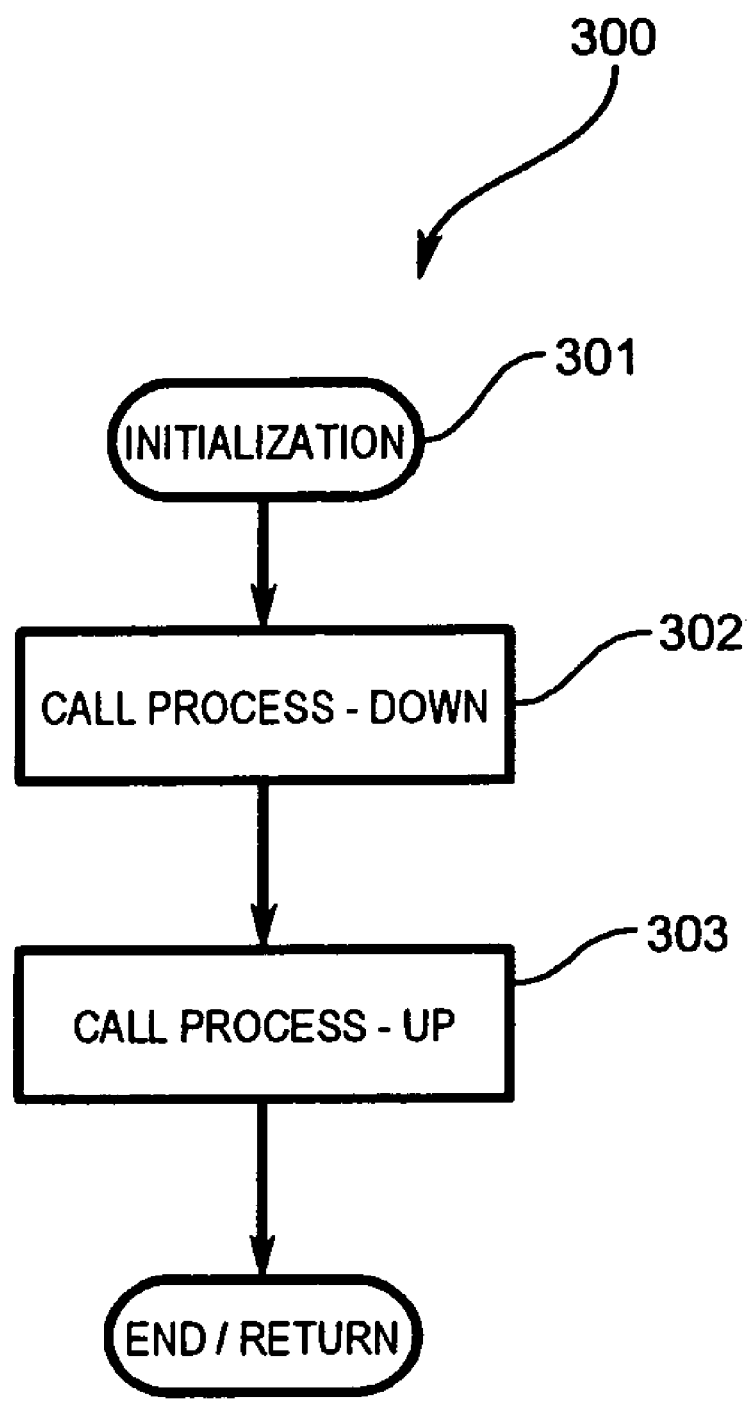
FIG. 3 is a flow chart showing the processing steps in recursive descent parsing method for identifying echo pulses in an echo profile.

Reference is made to FIG. 3, which shows in flowchart form a process 300 for identifying echoes and bumps in an echo profile. The first step in the process comprises an initialization step indicated by reference 301. The second step involves calling a process or function PROCESS_DOWN( ) as indicated in block 302. The third step represented by block 303 involves calling a process PROCESS_UP( ).

Figure 4:
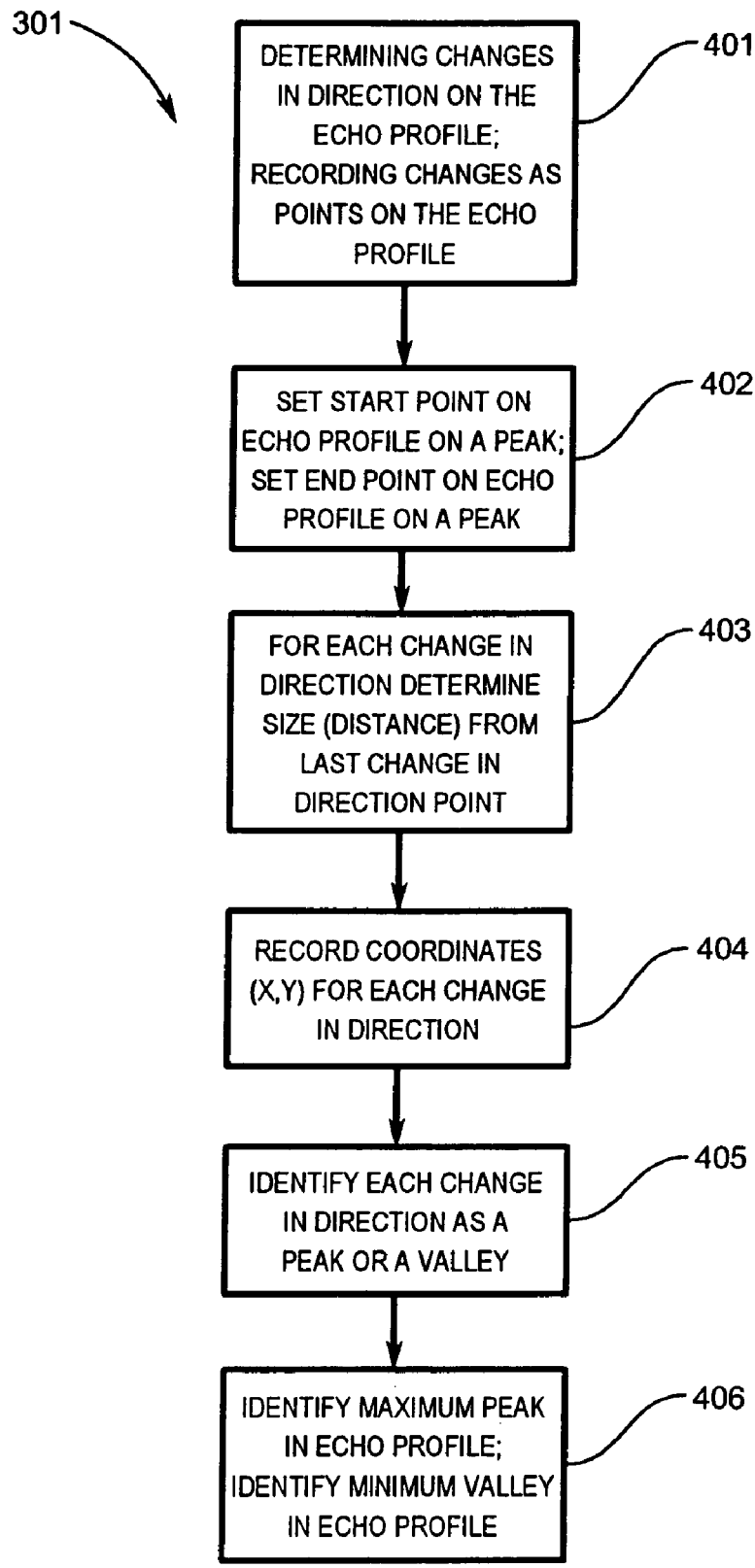
FIG. 4 is a flow chart showing the processing steps for the initialization operation of FIG. 3.

The initialization step 301 is shown in more detail in FIG. 4. The first operation 401 in the initialization step involves marking all changes in direction in the echo profile 200 and recording these changes as points on the echo profile 200. The next operation 402 in the initialization 301 involves starting the echo profile 200 at a peak and also ending the echo profile 200 at a peak. The echo profile 200 is started at a peak by forcing the first point in the echo profile 200 to be higher than the second point, if the condition is not already met. The echo profile 200 is ended at a peak by forcing the last point in the profile to be higher than the second last point. The next operation 403 in the initialization 300 involves determining, for each change in direction, the size (distance) from the point of the last change of direction to the point of the current change in direction is recorded. The next operation (block 404) involves recording x and y coordinates for each change in direction in the echo profile 200 (as determined in step 401). The next operation in block 405 involves identifying the change in direction as a peak (i.e. high point) or as a valley (i.e. low point). The final operation 406 in the initialization step 301 involves identifying the maximum peak in the echo profile 200 and the minimum valley in the echo profile.

According to another aspect of the invention, the echoes identified in the echo profile 200 are processed as half echoes. For example as shown in FIG. 2, the echo 202a comprises an UP half echo 204a and a DOWN half echo 206a. Similarly, the second 202b and third 202c echoes are processed using UP half echoes 204b and 204c and DOWN half echoes 206b and 206c, respectively. By processing the echoes 202 as half echoes, it is also possible to the ring down portion as a half echo, i.e. a DOWN half echo indicated by reference 210 in FIG. 2.

Reference is made back to FIG. 3, after the initialization operation, a call is made to the PROCESS_DOWN( ) function. The PROCESS_DOWN( ) function is used to process a DOWN half echo (for example, 210 or 206 for the echo profile 200 in FIG. 2) from the start of the echo profile to the minimum valley (with no parent) as determined in step 406 of the initialization procedure 301 (FIG. 4). The third step, as also shown in FIG. 3, comprises calling a function PROCESS_UP( ) to process an UP half echo (for example, 204a or 204c for the echo profile 200 in FIG. 2). The UP half echo is processed from the minimum valley (as determined in step 406 of the initialization process in FIG. 4) to the end of the echo profile with no parent.

The operation of the functions PROCESS_DOWN( ) and PROCESS_UP( ) is further described with the following pseudo code listings.

```
Pseudo code
© Siemens Milltronics Process Instruments Inc. 2002-2003
PROCESS_DOWN half echo:(input: start point, end point, parent echo)
        /* this is a recursive call */
        count the number of changes in direction between the start and end point supplied;
        if number of changes is zero, return; /* a DOWN half echo has been identified */
        identify the lowest valley between the start and end points; /* this divides the
        current down section into two parts */
        identify the last of the two parts; /* i.e. from the lowest valley to the end of the
        section */
        if there is no parent echo
                then
                        create a parent DOWN half echo from the supplied start and end points;
        else
                use the parent supplied;
        call PROCESS_BUMP(input: start, end, parent)
        /* to identify the bump between the lowest valley and the end of the DOWN section
        based on the parent down half echo supplied */
        /* where:
                start = lowest valley
                end = end of current down half echo
                parent is current down half echo */
        if the second section is identified as a distinct BUMP,
                then
                                that BUMP is separated from the current DOWN section, and the
                                first section from the supplied starting point to the start of this BUMP
                                is reprocessed
                                a recursive call is made to PROCESS_DOWN half echo with the
                                same start point, the lowest valley (i.e. start of the separated BUMP)
                                and the same parent
                else
                        if a RIPPLE is identified
                        then
                                the two direction changes that make up this ripple are
                                eliminated,
                                and
                                a recursive call is made using the same parameters;
                                /* the difference is that one RIPPLE has been eliminated */
                return the results of either of these recursive calls.
PROCESS_UP half echo(input: start point, end point, parent echo)
        /* this is a recursive call */
count the number of changes in direction between the start and end point supplied:
if number of changes is zero, then return;/*a UP half echo has been identified */
identify the highest peak between the start and end points; /* This divides the
current down section into two parts */
identify the last of the two parts, from the highest peak to the end of the section;
if there is no parent echo
        create a parent UP half echo from the supplied start and end points;
else
        use the parent supplied;
call PROCESS_BUMP(input: start, end, parent)
/* to identify the bump between the highest peak and the end of the UP section
based on the parent up half echo supplied */
/* where:
        start = highest peak
        end = end of current up half echo
        parent is current up half echo */
if the second section is identified as a distinct BUMP,
        then
                that BUMP is separated from the current UP section, and
                the first section from the supplied starting point to the start of this
                BUMP is reprocessed;
                a recursive call is made to PROCESS_UP half echo with the same
                start point, the highest peak (i.e. start of the separated BUMP) and
                the same parent
        else
                If a RIPPLE is identified,
                then
                        the two direction changes that make up this ripple are
                        eliminated,
                        and
                        a recursive call is made to PROCESS_UP using the same
                        parameters;
                        /* the difference is that one RIPPLE has been eliminated */
                return the results of either of these recursive calls.
It will be appreciated that the PROCESS_UP function is also recursive call and is almost
identical to PROCESS_DOWN half echo. The difference is that the UP side of a BUMP is
processed, otherwise the process or function is implemented in the same way.
```

-continued

PROCESS_BUMPS
    This routine is a combination of the functions PROCESS_DOWN half echo and PROCESS_UP half echo. The combination of the two defines a BUMP or an ECHO The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method for generating an echo profile in a time-of-flight ranging system, said method comprising the steps of:
    transmitting a transmit burst of energy to a reflective surface;
    receiving reflected pulses from said reflective surface, and converting said reflected pulses into echo signals for the echo profile;
    performing recursive descent parsing on said echo profile;
    determining one or more echoes in said echo profile through said recursive descent parsing.

2. The method as claimed in claim 1, wherein said step of performing recursive descent parsing comprises characterizing the echo profile into peaks and valleys, wherein said peaks start or end at a valley.

3. The method as claimed in claim 2, wherein said peaks are further characterized in terms of bumps, and said recursive descent parsing is applied to said bumps, said recursive descent parsing of said bumps comprises recursively processing said bumps to identify bumps which cannot comprise valid echoes in the echo profile.

4. The method as claimed in claim 3, wherein said recursive processing of said bumps comprises identifying bumps as noise in the echo profile and eliminating those identified bumps from further consideration as a potential echo.

5. The method as claimed in claim 2, further comprising the step of partitioning said peaks into corresponding up half peaks and down half peaks, each said up half peaks starting on a corresponding valley, and each of said down half peaks ending on a corresponding valley.

6. The method as claimed in claim 5, wherein said peaks are further characterized in terms of bumps, and said recursive descent parsing is applied to said bumps to identify bumps which cannot comprise valid echoes.

7. The method as claimed in claim 6, wherein said recursive descent parsing of said bumps comprises identifying bumps as noise in the echo profile and parsing those identified bumps from further processing.

8. A method identifying echoes in an echo profile for a time-of-flight ranging system, said method comprising the steps of:
    transmitting a transmit burst of energy to a reflective surface;
    receiving reflected pulses from said reflective surface, and converting said reflected pulses into potential echoes in the echo profile;
    performing recursive descent parsing on the echo profile to identify valid echoes in the echo profile and eliminate invalid echoes from the echo profile.

9. The method as claimed in claim 8, wherein said step of performing recursive descent parsing comprises characterizing the echo profile as comprising a plurality of peaks and a plurality of valleys, each of said peaks beginning at a valley and ending at a valley.

10. The method as claimed in claim 9, wherein said step of characterizing the echo profile as comprising peaks and valleys comprises the steps of:
    determining changes of direction in the echo profile;
    for each of said changes of direction determining a size for said change of direction in relation to the last change in direction;
    recording coordinates for each of said changes in direction;
    characterizing each of said changes of direction as a peak or as a valley based on said coordinates and said size.

11. The method as claimed claim 10, further including the step of identifying a maximum peak from said plurality of peaks and the step of identifying a minimum valley from said plurality of valleys.

12. The method as claimed in claim 11 further including the step of setting a start point for parsing on one of the peaks in the echo profile, and the step of setting an end point on another of the peaks in the echo profile.

13. The method as claimed in claim 10, further including the step of partitioning each of said peaks into an up half peak and a down half peak.

14. The method as claimed in claim 13, wherein said peaks are further characterized as bumps, and said recursive descent parsing is applied to said bumps to identify noise in the echo profile and eliminate the associated bumps from further consideration as potential echoes.

15. The method as claimed in claim 13 wherein one of said half peaks corresponds to a ring down section in the echo profile.

16. A level measurement device for measuring a distance to a material having a surface, said level measurement device comprising:
    a transducer for emitting energy pulses and detecting energy pulses reflected by the surface of the material;
    a controller having a receiver and a transmitter;
    said transducer having an input port operatively coupled to said transmitter and being responsive to said transmitter for emitting said energy pulses, and said transducer including an output port operatively coupled to said receiver for outputting reflected energy pulses coupled by the transducer;
    said receiver including a converter for converting said reflected energy pulses into signals;
    said controller including a program component for generating an echo profile based on said signals, said echo profile comprising potential echoes and potential noise;
    said controller including another program component for performing recursive descent parsing on said echo profile and for identifying one or more echoes in said echo profile.

17. The device as claimed in claim 16, wherein said recursive descent parsing component includes a program component for characterizing said echo profile into peaks and valleys.

18. The device as claimed in claim 17, wherein said peaks are further characterized in terms of bumps, said recursive descent parsing component recursively processes said bumps to identify bumps which cannot comprise valid echoes in the echo profile.

19. The device as claimed in claim 18, wherein said recursive descent parsing component includes a program component for partitioning said peaks into corresponding up half peaks and down half peaks, each said up half peaks starting on a corresponding valley, and each of said down half peaks ending on a corresponding valley.

20. The device as claimed in claim 19, wherein one of said half peaks corresponds to a ring down section in the echo profile and said recursive descent parsing component includes a program component for processing potential echoes in said ring down section.

21. A time of flight ranging system comprising:
a transducer for emitting energy pulses and detecting reflected energy pulses;
a controller having a receiver and a transmitter;
said transducer having an input port operatively coupled to said transmitter and being responsive to said transmitter for emitting said energy pulses, and said transducer including an output port operatively coupled to said receiver for outputting reflected energy pulses coupled by the transducer;
said receiver including a converter for converting said reflected energy pulses into electrical signals;
said controller including a program component for generating an echo profile based on said electrical signals, said echo profile comprising potential echoes and potential noise;
said controller including another program component for performing recursive descent parsing on said echo profile and for identifying one or more echoes in said echo profile.

* * * * *